United States Patent
Büchler et al.

(10) Patent No.: US 7,492,470 B2
(45) Date of Patent: Feb. 17, 2009

(54) METHOD FOR THREE-DIMENSIONAL SHAPE MEASUREMENT OF A BODY

(75) Inventors: Erik Büchler, Frankfurt am Main (DE); Hartmut Brinkmann, Bohmte (DE); Andre Garthaus, Osnabrueck (DE); Philip Von Schroeter, Rodenbach (DE)

(73) Assignee: Degudent GmbH, Hanau (DE)

( * ) Notice: Subject to any disclaimer, the term of this patent is extended or adjusted under 35 U.S.C. 154(b) by 320 days.

(21) Appl. No.: 11/399,346

(22) Filed: Apr. 7, 2006

(65) Prior Publication Data
US 2006/0227338 A1    Oct. 12, 2006

(30) Foreign Application Priority Data
Apr. 8, 2005    (DE) .................... 10 2005 016 525

(51) Int. Cl.
*G01B 11/24* (2006.01)
*A61C 3/00* (2006.01)
(52) U.S. Cl. .............. 356/601; 356/603; 356/612; 356/625; 433/29; 433/215
(58) Field of Classification Search ......... 356/601–625; 433/29, 215; 33/514
See application file for complete search history.

(56) References Cited

U.S. PATENT DOCUMENTS

| | | | | |
|---|---|---|---|---|
| 4,907,251 A | * | 3/1990 | Mork et al. ................. 378/39 |
| 4,964,770 A | * | 10/1990 | Steinbichler et al. ......... 433/223 |
| 5,386,292 A | * | 1/1995 | Massen et al. .............. 356/603 |
| 5,548,405 A | * | 8/1996 | Motosugi .................... 356/601 |
| 5,569,578 A | * | 10/1996 | Mushabac .................... 433/215 |
| 5,760,906 A | * | 6/1998 | Sato .......................... 356/602 |
| 5,897,509 A | * | 4/1999 | Toda et al. .................. 600/589 |
| 6,334,773 B1 | * | 1/2002 | Ahlen et al. ................. 433/29 |
| 6,402,707 B1 | * | 6/2002 | Ernst .......................... 600/590 |
| 6,431,871 B1 | * | 8/2002 | Luthardt ..................... 433/223 |
| 6,750,971 B2 | * | 6/2004 | Overbeck et al. ........... 356/405 |
| 7,006,210 B2 | * | 2/2006 | Overbeck et al. ........... 356/138 |
| 2005/0234344 A1 | | 10/2005 | Sanilevici et al. | |

FOREIGN PATENT DOCUMENTS

| | | |
|---|---|---|
| DE | 4013309 | 10/1991 |
| DE | 4214876 | 11/1993 |
| DE | 4301538 | 7/1994 |
| DE | 69628956 | 5/2004 |

* cited by examiner

*Primary Examiner*—Sang Nguyen
(74) *Attorney, Agent, or Firm*—Dennison, Schultz & MacDonald

(57) ABSTRACT

The invention relates to a method for three-dimensional shape measurement of a body or of a part thereof, in particular of a dental object such as a model, by scanning non-contact distance measurement using an optical sensor device comprising a beam source, where the shape of the body subjects reproducing areas to a beam at various incidence angles (impinging beam), and the reflected beam (measuring beam) is measured, with the body being adjusted relative to the optical sensor device. To permit measurement with high precision of the body and undercuts thereof, without tilting being necessary, it is proposed that for shape measurement of the respectively measured area the beam (measuring beam) reflected therefrom, which describes an angle $\alpha$ to a surface normal corresponding to the respective area, is taken into account, said angle being equal to or smaller than a predefined critical angle $\alpha_{GR}$ relative to the surface normal.

14 Claims, 4 Drawing Sheets

METHOD FOR THREE-DIMENSIONAL SHAPE MEASUREMENT OF A BODY

The invention relates to a method for three-dimensional shape measurement of a body or of a part thereof, in particular of a dental object such as a model, by scanning non-contact distance measurement using an optical sensor device, where the shape of the body subjects reproducing areas to a beam at various incidence angles (impinging beam), and the reflected beam (measuring beam) is measured, with the body being adjusted relative to the optical sensor device.

A corresponding method is known from DE-A-43 01 538, using which denture models in particular are measured. To do so, at least two light stripe sensors are provided that measure the denture from various angles according to the triangulation principle. The appropriate measurement results are then digitized in order to manufacture a denture using CAD/CAM methods on that basis.

DE-A-101 33 568 also shows a method of three-dimensional measurement for digitizing a body, in particular a dental object. To do so, the body is clamped in a holder in a defined orientation, the body is subjected to a beam and the reflected beam is evaluated, with the body being moved both translatorally and rotatorally relative to a beam source for measurement. This beam source is in particular a stripe light scanner.

From DE-A-42 14 876 a method for optical measurement of teeth is known, in which tooth coordinates are corrected by means of correction values. In doing so, the surface normal of a measuring point is considered.

For the optical examination of a specimen DE-A-40 13 309 provides that a laser beam impinges a specimen surface for then determining the radiation from a CCD camera reflected in parallel to the surface normal.

From DE-T-696 28 956 a device for scanning an object can be learned, whereby said device comprises a laser light source. To be moved by an operator, the scanning device is mounted on a multi-flexible arm.

The problem underlying the present invention is to develop a method of the type described at the outset such that shape measurement of a body, in particular undercuts thereof, can be performed simply, with the effort of moving the body relative to the beam source being kept low. At the same time, precise measurement should be made possible.

To solve the problem, the invention substantially provides that the body is subjected to the beam emitted by the optical sensor device at various incidence angles (impinging beam), and that a beam (measuring beam) reflected along the incident beam is measured depending on the various reflection angles in order to ascertain the distance using the optical sensor device, and that for shape measurement of the respectively measured area the beam (measuring beam) reflected therefrom, which describes an angle $\alpha$ to a surface normal corresponding to or assigned to the respective area, is taken into account, said angle being equal to or smaller than a predefined critical angle $\alpha_{GR}$ relative to the surface normal, whereby for the shape measurement reflected beam remains unconsidered, the angle of which relative to the surface normal is greater than the predefined critical angle $\alpha_{GR}$.

It is especially provided by the invention
that the body is subjected to the beam emitted from the optical sensor device at various incidence angles (impinging beams),
that a beam reflected in the opposite direction of the incident beam is measured in order to ascertain the distance using the optical sensor device,
that for each measured area it is controlled whether a beam reflected out of it to a surface normal corresponding to or assigned to the respective area, defines an angle $\alpha$ being equal to or smaller than a predefined critical angle $\alpha_{GR}$ that reflected beam not fulfilling this condition is no longer evaluated.

To determine the surface normal, it is provided here that the normal or a mean normal of an area is calculated from the measurement data of the area obtained from the reflected beam, in order to then take into account, during calculation of the shape of the area, i.e. its surface contour, only that measurement data to which is assigned a measuring beam with a reflection angle describing, with the previously calculated (mean) surface normal, an angle smaller than or equal to the predefined critical angle $\alpha_{GR}$. The critical angle $\alpha_{GR}$ is preferably in the range between 10° and 20°.

A cause for determining $\alpha_{GR}$ is that due to the deflection of the emitted beam a distortion takes place, i.e. an outgoing beam with a dot-shaped or circular cross-section is for example imaged as an ellipse or line on the surface at the point to be measured. This causes measurement falsification. To permit only measurement values having low distortion for calculation of the shape, $\alpha_{GR}$ is determined.

In other words, from a cluster of measurement data or points representing an area to be measured, first the normal is determined, in order to then filter out the measurement data to be used so that as a result only that data which leads to a shape measurement of the area satisfying the set accuracy requirements is taken into account.

Here, each measurement point represents a space coordinate, where the z coordinate is determined using the optical sensor device preferably designed as a distance sensor, whereas the x and y coordinates are predefined by the position of the object. In order to eliminate distortions relative to the x, y coordinates caused by the three-dimensional geometry of the body to be measured, a coordinate transformation takes place beforehand on the basis of a standardized test body that is preferably a sphere or a spatial body having a known geometry.

To set various incidence angles, it is provided that the beam emitted by the optical sensor device is deflected using at least one deflection element such as a mirror or prism. In particular, it is provided that a mirror arrangement rotatable about one axis is arrangeable in the path of the beam in order to permit setting of required angles both vertical to the x/y plane within which the body is adjustable and diverging from 90° relative to the plane. Other deflection means such as prisms are also possible.

With these measures, a partial shape measurement from various views of the body is possible using the deflection means used, such as mirror or prism. At the same time, the body is adjusted in the x/y plane in order to determine for every required x/y position the z position of the body by means of the measuring beam reflected by the body. This then provides the space coordinate of the measurement point. The x, y and z values for every surface measurement point are ascertained accordingly.

By using deflection means, it is possible to optically measure undercut without having to tilt the body. As a result, shape measurement can be achieved with mechanically simple measures.

The partial shape measurement is optically distorted by the deflection of the beam. To achieve a correction, i.e. a rectification of the individual views, a reference object is measured, i.e. scanned beforehand, where for the respective position of the deflection element such as a mirror a comparison with the geometrical data of the reference object takes place and thus permits a transformation which ensures that the measurement values in the actual space coordinates of the predefined space coordinate system are ascertained. The individual views are then combined into an overall picture and hence into the three-dimensional shape of the body to be measured.

In a noteworthy embodiment of the invention, it is provided that the object is aligned before the scanning measurement on a template spanning a surface which runs transversely, preferably vertically, to the plane created by the beam emitted by the optical sensor device and deflected by the respective reflection element. In particular, the template should be aligned such that the surface is parallel to the beam emitted by the sensor device before the beam is deflected. The alignment of the body in the z direction relative to the template is such that the body contacts the surface in at least one point, preferably in at least two areas at a distance from one another.

This measure ensures that the body to be measured is optimally aligned relative to the z axis, which is measured using the measuring beam and the optical sensor device. Before this, the body such as a negative or positive dental model is fastened to a model holder which in turn extends from a measuring table adjustable in the x and y directions of the coordinate system.

It is proposed in a embodiment inventive per se that an overall image is made of the body to be measured before the actual scanning measurement in order to define scan areas which are measured according to a required scan strategy. A corresponding and in particular two-dimensional overall image can be recorded with a separate optical sensor—if necessary however also using the optical sensor device—where the image is displayable on a monitor. In the overall image, the user then defines the scan area(s) using an input device. This can be achieved in MS Word for example with a mouse by opening a rectangle and with "Drag" and "Zoom" to define the measurement area. Furthermore, the scan areas are classified. In the case of dental objects, the restoration type or the geometrical structure for each scan area can be defined using the input device in accordance with special dental nomenclature. For example, after defining a rectangle the restoration type can be selected from among the possible preselections such as cap, inlay, onlay, crown, bridge abutment, pontic, implant, gingiva, adjacent tooth, ready-made, partially ready-made or individualized abutments (posts) etc.

For each scan area, the scan strategy is defined taking into account the restoration type or the specified geometrical structure and selected automatically out of several scan strategies previously filed in a computer. For each scan area, the x/y traverse paths of the measuring table are calculated, and the selection of deflection elements such as mirrors is decided. Calibration by scanning of a calibration element such as a calibration sphere took place beforehand for the respective x/y measurement values.

The impinging and hence measuring beam used for measurement must not necessarily have a dot-like or circular cross-section. A linear or area cross-section is equally possible. There is no falsification of the measurement values as a result, since an identical impinging beam was used for calibration, i.e. during scanning of the calibration element.

Calibration does not necessarily have to be performed before each measurement. Positioning is followed by measurement, i.e. scanning, of the selected area of the body, where following the teachings in accordance with the invention only those measurement values are taken into account that are obtained from measuring beams which do not exceed a pre-determined critical angle $\alpha_{GR}$ relative to the surface normal of the area with regard to the body area to be measured.

By means of the teachings in accordance with the invention, individual areas of a body whose shapes are to be recorded are scanned, with the x/y coordinates of the respective measurement points being determined by the position of the measuring table, which is adjusted relative to the optical sensor device, and the z coordinates by the optical sensor device itself. For every area to be measured, i.e. scanned, first the deflection angle of the emitted beam is determined and then the body is moved into the x/y positions corresponding to the required measurement points. The measurements are performed here such that overlap areas occur, i.e. edge areas of individual areas for measurement are measured at various deflection angles and hence impingement and reflection angles. Measurement points assigned in these overlap areas to measuring beams whose reflection angles relative to the respective surface normal of the respectively measured area do not exceed the predefined or determined critical angle $\alpha_{GR}$ can then be selected such that only those points ascertained from measuring beams describing a smaller angle relative to the respective area surface normal are further processed.

After measurement of all areas and the total shape measurement calculated therefrom, the appropriately digitized data is sent to a CAD/CAM software for further processing, for example in order to permit manufacture of a required denture in the dental field.

Fully general, it can be measured with one measuring beam which is reflected to the impinging beam in opposite direction, i.e. impinging beam and measuring beam describe an angle unequal to 0°. If it is provided for preference that the measuring beam is reflected back into the impinging beam, as is typically the case in laser distance measurements or in conoscopic measurements, it is of course also possible to perform a z coordinate measurement using the triangulation method. Preferably however, a laser distance measurement is performed with the aid of a laser beam in order to determine the z coordinate.

Further details, advantages and features of the invention are shown not only in the claims and in the features they contain—singly and/or in combination—but also in the following description of preferred embodiments shown in the drawing.

The teachings in accordance with the invention are explained using the example of shape measurement for a dental model, without this restricting the teachings in accordance with the invention. The dental model—whether this is a positive model or an impression (negative model)—is scanned in accordance with the teachings described below, in order to then make a required dental restoration from the data obtained and digitized using the CAD/CAM software. A method for making the denture can be used here as is known from WO-A-99/47065, to the disclosure of which express reference is made.

Figure 1:
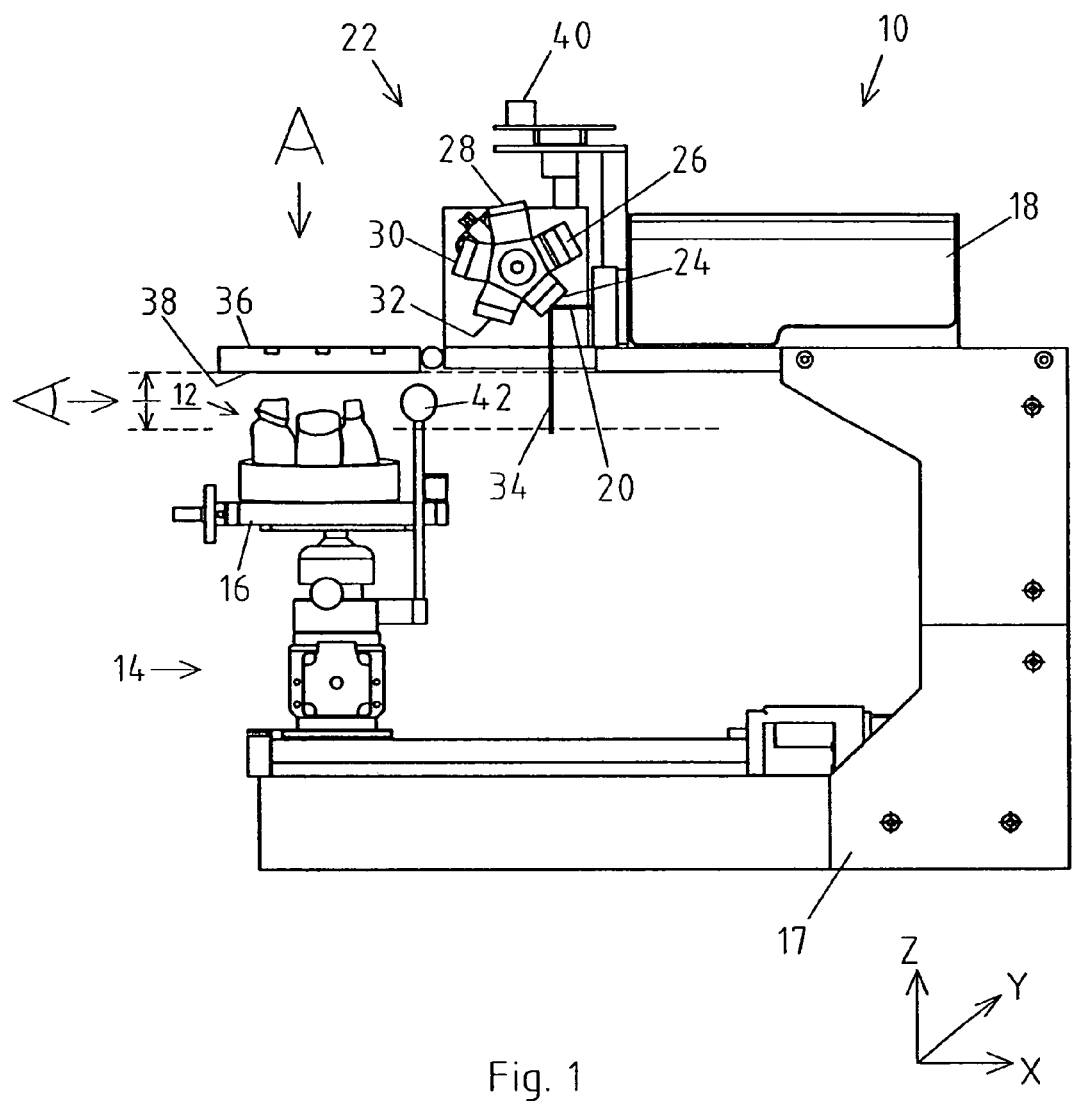
FIG. 1 shows a principle diagram of a measuring device.

FIG. 1 shows purely in principle a measuring unit 10 using which a dental model 12 is to be measured by scanning.

The unit 10 comprises a measuring table 14 movable in the x and y direction and on which the dental model 12 is mounted in a model holder 16, for example. The measuring table 14 is adjustable in the x and y directions along the guideways extending from a frame 17 of the unit 10. An optical sensor device is arranged above the measuring table 16 and preferably connected to the frame 17, designed in the embodiment as a laser distance sensor 18.

With the distance sensor 18, the z coordinates of areas of the model 12 are to be determined in the manner described in the following, i.e. a shape measurement by determining the space coordinates x, y and z. The x and y coordinates of the measurement point are predefined by the position of the measuring table 14.

The laser distance sensor 18 has a laser light source, not shown. In the optical path of the emitted beam 20 a mirror arrangement 22 of revolver-like design is arranged which in the embodiment comprises five mirrors 24, 26, 28, 30, 32. The mirrors 24, 26, 28, 30, 32 have, relative to the optical axis of the light source, i.e. to the emitted beam 20, different inclination angles in regard to the x and y planes. The beam 34 reflected from the respective mirror—in the embodiment from mirror 24—then impacts the model 12 in a predefined x/y position. The beam reflected back by the model 12 into the deflected beam 34 and which is the actual measuring beam is then measured by the laser distance sensor 18 in order to determine in this way the z position of the impingement point of the deflected beam 34. So far however, reference has been made to sufficiently known measuring methods and evaluation possibilities that are known from coordinate measurement technology.

The reflection surface of the mirrors 24, 26, 28, 30, 32 is designed such that the deflected beam 34 also records undercuts of the model 12 to be measured. Hence the deflected beam 34 impacts, depending on the respectively used mirror 24, 26, 28, 30 or 32 or on its alignment to the beam 20 emitted by the laser distance sensor to the x/y plane at a required angle α, so that as a result undercuts of the model 12 can be measured without problem and without having to tilt the model 12. Instead, the model is adjusted exclusively in the x/y plane of the measuring unit 10 for setting the respective measurement point whose z coordinate is measured using the laser distance sensor 18.

In order to record measurement points of the model 12 over the entire depth of field T of the sensor 18, the model 12 is aligned before measurement on a template 36 having a reference surface 38 parallel to the x/y plane. Here the measuring table 16 is aligned relative to the template 36, i.e. to the reference surface 38, such that the model 12 contacts the surface 38. In the case of a model with which a cap or a crown is to be made, the model 12 will contact the surface 38 at one point. When bridges are made, the bridge abutments in the model will each contact the surface 38. With this pre-adjustment, it is visibly assured that the z measurement area of the laser distance sensor 18 can be used to the full.

Figure 2:
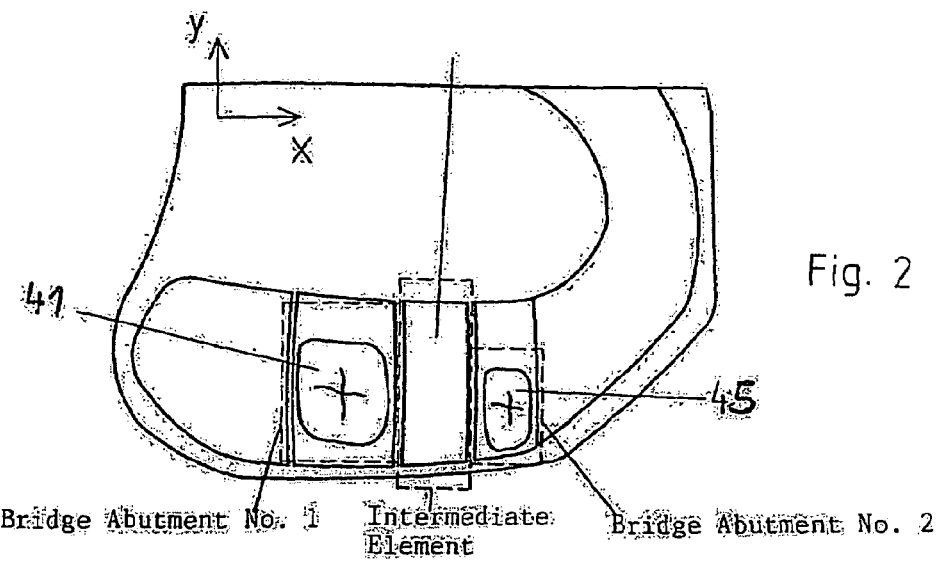
FIG. 2 shows an overall image of an object to be measured.

An overall image of the adjusted model 12 is then made preferably using a further optical sensor 40 such as a CCD camera. The overall image is displayed on a monitor in order for the user to then determine or define scan area. The principle for this is shown in FIG. 2. For example, in a model intended for the manufacture of a bridge, areas 41, 43, 45 of the overall image are fixed using an input device. This can be achieved in MS Word with a mouse by opening a rectangle and with "Drag" and "Zoom" to define the measurement area 41, 43, 45. Then a restoration type or a geometrical structure in accordance with special dental nomenclature for the respective measurement area 41, 43, 45 can be determined using an input device. In the embodiment, the measurement area 41 is defined as restoration type bridge abutment No. 1, measurement area 43 as intermediate element, and measurement area 45 as restoration type bridge abutment No. 2. Then the scan strategy is fixed on the basis of the measurement area and of the defined restoration type or geometrical structure in accordance with data filed in a computer. By scan strategy is meant that for every scan area 41, 43, 45 the traverse paths of the measuring table 14 in the x and y directions and the measurement point density are defined. Furthermore, there is a subdivision of the respective total measurement area 41, 43, 45 into discrete areas which are each defined with different impingement angles, i.e. different deflection of the emitted beam by setting of different mirrors 24, 26, 28, 30, 32. It is of course possible to dispense with subdivision of the respective measurement area 41, 43, 45 and to subject each respective measurement area 41, 43, 45 completely to variously deflected impinging beams.

Figure 3:
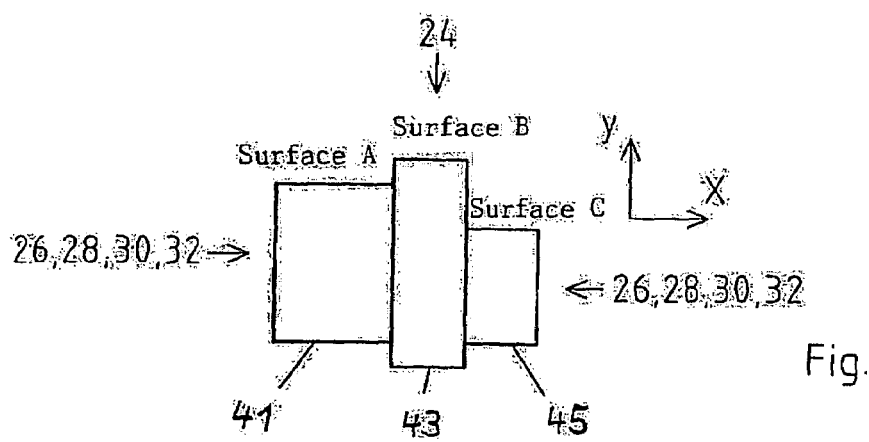
FIG. 3 shows scan areas of the object according to FIG. 2.

The measurement areas 41, 43, 45 as per FIG. 2 and shown in principle in FIG. 3 are subjected to light deflected by means of different mirror positions.

For example, in the embodiment the measurement area 41 and hence the surface A is subjected to a beam consecutively, taking into account the respective x/y position, using the following mirrors:

Mirror 26 for an oblique light incidence in the x axis direction

Mirror 28 for an oblique light incidence in the −x axis direction

Mirror 30 for an oblique light incidence in the y axis direction

Mirror 32 for an oblique light incidence in the −y axis direction

The measurement area 45 and hence the surface C are measured in the same way. The surface B (measurement area 43) is measured exclusively using the beam deflected by the mirror 24 and vertical to the x/y plane, i.e. corresponding to the beam 34.

The measurement point density of the respective measurement area 41, 43, 45 is also defined by the scan strategy and determined by the required measurement precision.

In order to correct during partial shape measurement the optical distortion caused by the mirrors, the laser distance sensor 18 is calibrated beforehand. To do so, a calibration element, in the embodiment in FIG. 1 a calibration ball 42, is provided which is measured for each mirror setting. This permits a transformation of the actual x/y/z coordinates of the measured point to the real position in the x/y/z coordinate system, which is incorporated into the measurements of the model 12.

In order to take into account only the measurement points, i.e. the x, y and z coordinates that represent with sufficient precision the shape of the model 12, the measurement data is identified and filtered as follows.

Figure 5:
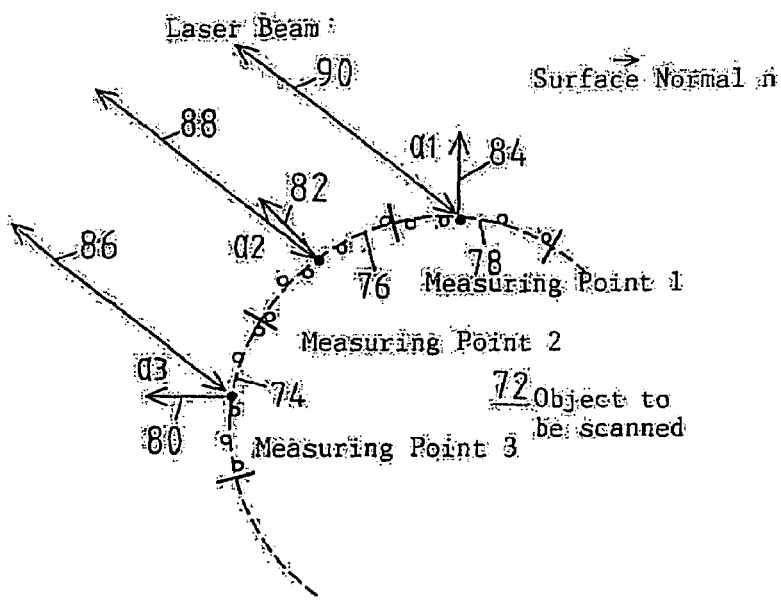
FIG. 5 shows a principle diagram to illustrate the measurement data evaluation.
Figure 4:
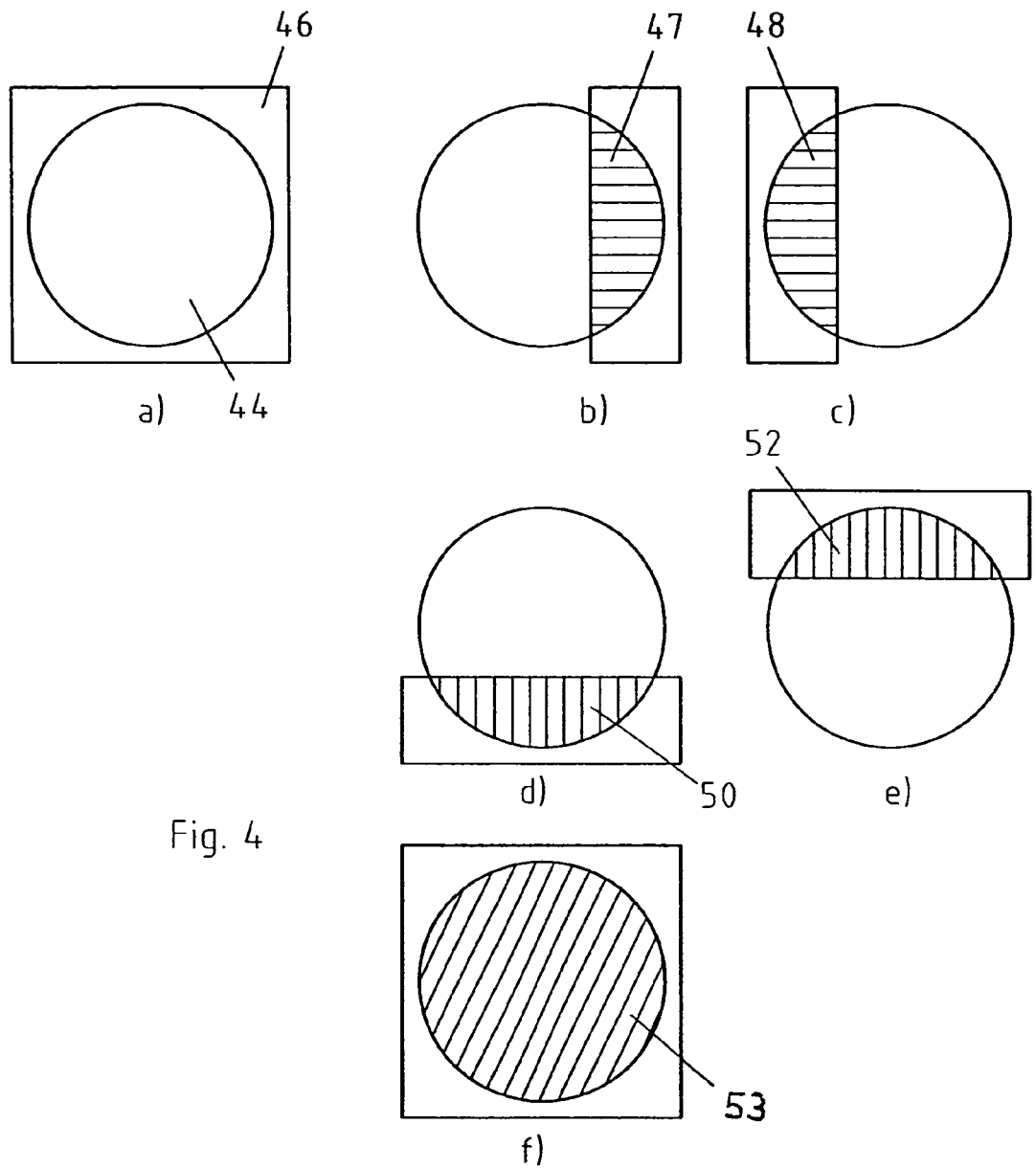
FIGS. 4a-4h show diagrams to illustrate the measurement principle.
Figure 4:
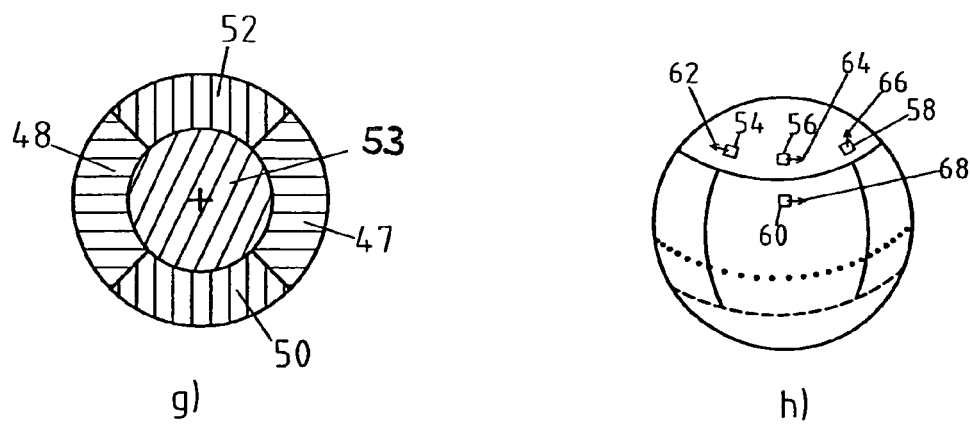

The selection and filtering of the measurement data is explained in principle using FIGS. 4 and 5. In FIGS. 4a) to 4f) it is first shown which partial areas of an object 44 are to be measured with which mirrors 24, 26, 28, 30, 32. In the embodiment, the object 44 is a sphere. In accordance with the previously provided explanations, first the scan area 46 to be assigned to the object 44 was defined, Then a part-area of the scan area 46 and hence a section 47 (hatched) of the surface of the sphere 44 is measured in accordance with FIG. 4b), in the embodiment using the mirror 26, which measures in the x axis direction with inclined angle of incidence. Then the part-area 48 containing the section 48 is measured with the mirror 28 in the −x axis direction, This is followed by measurement of the section 50 with the mirror 30 with inclined angle of incidence in the y axis direction. The section 52 shown in FIG. 4e) is measured with the mirror 32 with inclined angle of incidence in the −y axis direction. Finally measurement with the mirror 24 vertical to the x/y plane takes place (hatched area 53) in accordance with FIG. 4f).

The measurement data of sections 47, 48, 50, 52, 53 is then linked up, as indicated in principle in FIG. 4g), in order to ascertain from the measurement values/data the shape of the object 44, as reproduced in FIG. 4h) in a 3D view.

In order to take account only of those measurement values which are sufficiently precise, selection and hence filtering is performed in the manner described below.

The respective area of the measured object 44 is subdivided into discrete areas or planes of which some are indicated purely as examples in FIG. 4h) and identified with 54, 56, 58, 60. A normal 62, 64, 66, 68 is calculated on the basis of the measurement values from every discrete part-area 54, 56, 58, 60. Only those measurement values of the respective discrete part-area 54, 56, 58, 60 are taken into account for determining the shape of the object 44 which have measuring beams assigned to them which describe an angle relative to the respective normal 62, 64, 66, 68 that is smaller than a predefined critical angle $\alpha_{GR}$. This is shown in principle by FIG. 5. For example, a measurement area of an object 72 to be measured is subdivided into discrete part-areas 74, 76, 78. To each discrete part-area 74, 76, 78 is assigned a mean normal 80, 82, 84 which is as already mentioned calculated from the measurement data of the respective part-areas 74, 76, 78. Then the associated measuring beam 86, 88, 90 is evaluated, for each measurement point of the discrete part-area 74, 76, 78 to which is assigned the normal 80, 82, 84, as to whether the angle $\alpha 1$, $\alpha 2$, $\alpha 3$ relative to the normal 80, 82, 84 is equal to or less than or greater than a predefined critical angle $\alpha_{GR}$. The measuring beams and hence the measurement points in which the angle $\alpha$ is greater than the predefined critical angle $\alpha_{GR}$ are ignored, while the measurement points of the measuring beams describing an angle $\alpha \leq \alpha_{GR}$ relative to the respective normal are evaluated in the calculation of the object 72, i.e. in shape measurement. Preferably is $30° > \alpha_{GR}$, particularly $10° > \alpha_{GR}$.

In FIG. 5, the measurement points which are the basis for calculation of the normals 80, 82, 84 shown as an open circle, whereas the measurement points classified in the manner described above are indicated by a closed circle. Furthermore, the illustration in FIG. 5 shows that the impinging beam and the measuring beam coincide.

Figure 6:
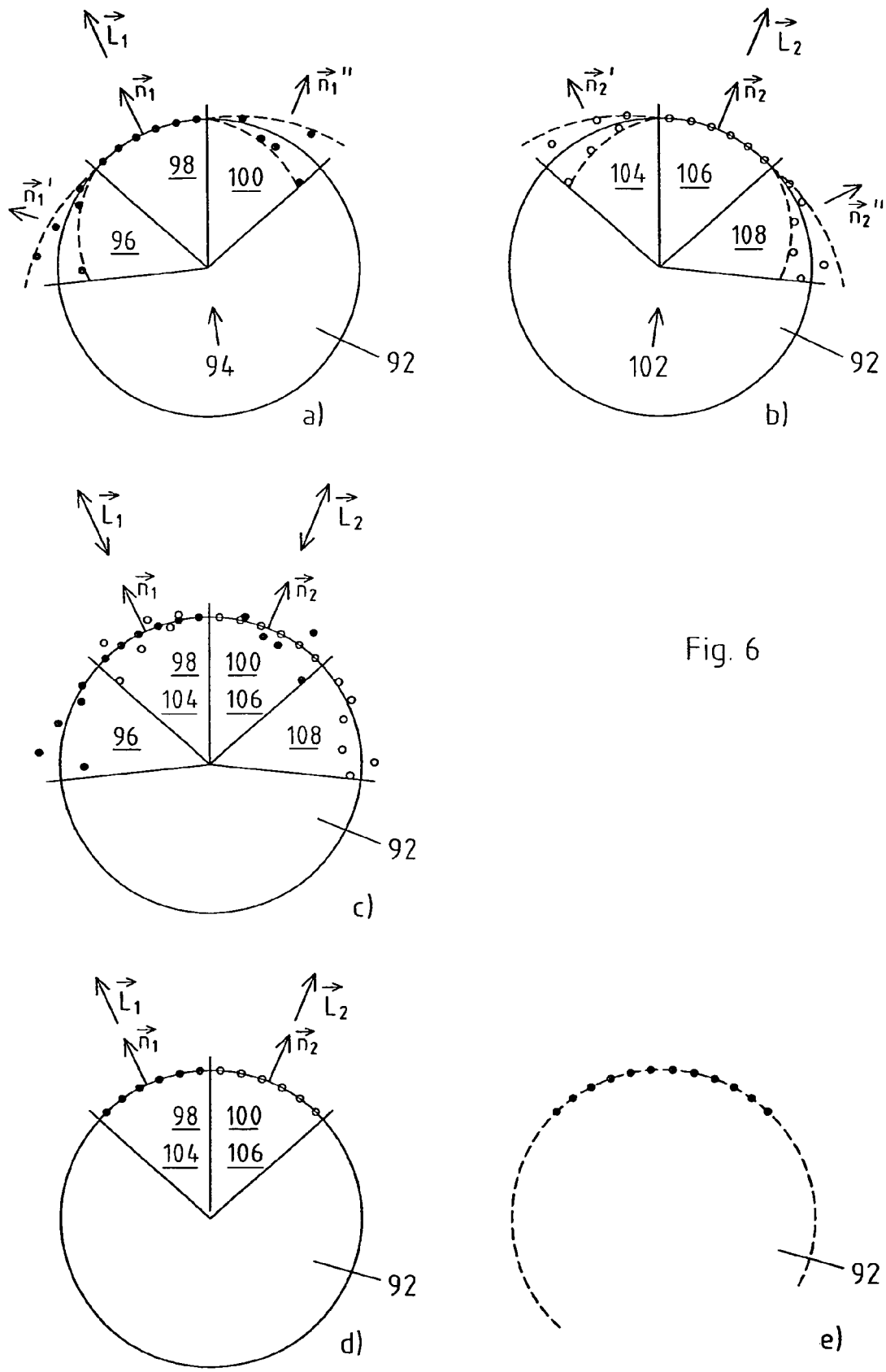
FIGS. 6a-6e show further principle diagrams to illustrate the measurement data evaluation.

The method in accordance with the invention for selecting and filtering measurement values is also made clear using FIG. 6, which shows measurement points ascertained using the measuring beams L1 or L2 which, depending on the divergence from the normal n1 or n2 assigned to the respective area, represent with varying precision the shape of the body 92 to be measured, which is a sphere in the embodiment. The measuring beam L1 is thus used to measure a total area 94 which is subdivided into part-areas 96, 98, 100. Each part-area 96, 98, 100 is assigned a normal n1, n1' and n1" calculated from measurement values measured in the respective area 96, 98, 100. Then the angle between the measuring beam L1 and the respective normal n1, n1' and n1" is determined. If the angle is outside the critical angle $\alpha_{GR}$, the appropriate measurement data is filtered out and hence not taken into account when calculating the shape of the body. In the embodiment in FIG. 6a), only the measurement data of area 98 is processed.

In FIG. 6b), a measuring beam L2 that diverges in direction from the measuring beam L1 is used for measurement of the body 92. In line with the explanation in FIG. 6a), the entire measured area 102 us subdivided into discrete areas 104, 106, 108, and each area is assigned a normal n2, n2' and n2" from the measurement data obtained. The angle difference between the measuring beam L2 and the respective normal n2, n2' and n2" is then determined. In the embodiment in FIG. 6b), only the measurement data of area 106 is taken into account.

The measurements of the areas 96, 98, 100, 104, 106, 108 result overall in a cluster of measurement data shown in FIG. 6c). The part-areas 98, 104 and 100, 106 match here. It can be seen that from the entire measurement data, taking into account the previously stated selection criterion regarding the critical angle between part-area normal and measuring beam according to FIG. 6d), only that measurement data which has been measured in the area 98, 104 with the measuring beam L1 and in the area 100, 106 with the measuring beam L2 is evaluated as sufficiently precise, since the measuring beam describes relative to the normal n1 or n2 assigned to the area 98, 104 or 100, 106 an angle smaller than the critical angle. The shape of the body is then calculated from the measurement data. It can be seen from FIG. 6e) that the processed measurement data reproduces the measured body 92 with sufficient precision. The digitized measurement data is then processed with a suitable software for subsequent manufacture of a required body with a CAD/CAM method.

It should be noted that the teachings in accordance with the invention for shape measurement can be performed in particular by means of a single optical sensor device if the sensor for the overall image is omitted. Of course the teachings in accordance with the invention are not departed from even if more than one sensor device is used for measurement of the z coordinate.

The invention claimed is:

1. A method for three-dimensional shape measurement of a body or of a part thereof by scanning non-contact distance measurement using an optical sensor device, comprising the steps of:
    subjecting an area of the body to an impinging beam emitted by the optical sensor device at various incidence angles, creating a measuring beam reflected opposite to the impinging beam,
    measuring the reflected beam, with the body being adjusted relative to the optical sensor device depending on angle of reflection in order to ascertain a distance using the optical sensor device,
    determining the shape of the measured area, taking into account the measuring beam which describes an angle $\alpha$ to a surface normal corresponding to or assigned to the measured area, said angle being equal to or smaller than a predefined critical angle $\alpha_{GR}$ relative to the surface normal, and not taking into account an angle x to a surface normal corresponding to or assigned to the measured area which is greater than the predefined critical angle $\alpha_{GR}$, and
    obtaining a data set representing the shape, which data set may be inputted to software for further processing.

2. Method according to claim 1, wherein the surface normal of the area to be measured is ascertained from unfiltered measurement data of the area obtained from the reflected beam, and the measurement data where the reflection angle is greater than $\alpha_{GR}$ is ignored for shape measurement.

3. Method according to claim 1, wherein the various incidence angles are set by deflection of the emitted beam using at least one deflection element.

4. Method according to claim 1, wherein the body or its surface to be measured is subdivided into discrete surfaces forming areas, and wherein on the basis of space coordinates of the discrete area calculated from the measuring beam reflected from the respective discrete area, the normal or mean normal thereof is calculated.

5. Method according to claim 1, wherein the object is aligned before the scanning on a template spanning a surface which runs transversely to a plane created by the beam emitted by the optical sensor device and deflected by a reflection element.

6. Method according to claim 5, wherein the template is aligned such that the surface is parallel to an undeflected beam emitted by the optical sensor device.

7. Method according to claim 5, wherein the body is aligned in a z-direction relative to the template such that the body contacts the surface in at least one point.

8. Method according to claim 5, wherein a two-dimensional overall image of the body aligned relative to the template is displayed on a monitor of a computer and the overall image is then subdivided into scan areas on the monitor.

9. Method according to claim 8, wherein a geometrical structure is assigned to the scan areas and under consideration of the scan areas traverse paths of the body, in an x/y direction and/or deflection angles of the emitted beam are defined to create a scan strategy, taking said structure into account.

10. Method according to claim 9, wherein the scan strategy is selected from several scan strategies previously filed in a computer.

11. Method according to claim 1, wherein the body is recorded before scanning measurement with the optical sensor device to obtain an overall image, and scan areas are then defined on the basis of overall image.

12. Method according to claim 1, wherein an impinging beam of dot, circle, linear or area cross-section is used.

13. Method according to claim 1, wherein as the reflected beam the beam is measured, a beam which is reflected into the impinging beam is measured.

14. Method according to claim 1, wherein the measuring beam describes an angle $\beta$ with $\beta$ unequal to 0° relative to the impinging beam in an impingement point of the body to be measured.

* * * * *